(12) United States Patent
Bluecher et al.

(10) Patent No.: US 12,257,138 B2
(45) Date of Patent: Mar. 25, 2025

(54) MULTIFUNCTIONAL TEXTURED DEVICE

(71) Applicant: BvW Holding AG, Cham (CH)

(72) Inventors: Lukas Bluecher, Eurasberg (DE); Michael Milbocker, Holliston, MA (US)

(73) Assignee: BVW Holding AG, Cham (CH)

( * ) Notice: Subject to any disclaimer, the term of this patent is extended or adjusted under 35 U.S.C. 154(b) by 19 days.

(21) Appl. No.: 16/690,701

(22) Filed: Nov. 21, 2019

(65) Prior Publication Data

US 2020/0155292 A1 May 21, 2020

Related U.S. Application Data

(60) Provisional application No. 62/770,575, filed on Nov. 21, 2018.

(51) Int. Cl.
*A61F 2/00* (2006.01)

(52) U.S. Cl.
CPC .... *A61F 2/0077* (2013.01); *A61F 2002/0081* (2013.01); *A61F 2002/0086* (2013.01); *A61F 2230/0006* (2013.01); *A61F 2230/0019* (2013.01); *A61F 2230/0021* (2013.01); *A61F 2230/0023* (2013.01); *A61F 2250/0014* (2013.01); *A61F 2250/0026* (2013.01); *A61F 2250/0037* (2013.01); *A61F 2250/0039* (2013.01)

(58) Field of Classification Search
CPC ............ A61F 2/0077; A61F 2002/0081; A61F 2230/006; A61F 2230/0019; A61F 2230/0008; A61F 2250/0026; A61F 2250/0037; A61F 2250/0039; A61F 2250/0014

See application file for complete search history.

(56) References Cited

U.S. PATENT DOCUMENTS

| | | | |
|---|---|---|---|
| 9,120,670 B2 | 9/2015 | Hulseman et al. |
| 9,908,274 B2 | 3/2018 | Hulseman et al. |
| 9,988,201 B2 | 6/2018 | Darin et al. |
| 10,022,227 B2 | 7/2018 | Jennissen |
| 10,377,044 B2 | 8/2019 | Hulseman et al. |

(Continued)

FOREIGN PATENT DOCUMENTS

| | | |
|---|---|---|
| CN | 104039368 A | 9/2014 |
| CN | 104321034 A | 1/2015 |

(Continued)

OTHER PUBLICATIONS

International Search Report and Written Opinion for corresponding PCT/US2019/062591, dated Mar. 13, 2020, 12 pages.

*Primary Examiner* — Dinah Baria
(74) *Attorney, Agent, or Firm* — Patterson Intellectual Property Law, P.C.; Ryan D. Levy; Mark A. Kilgore

(57) ABSTRACT

A device comprising a microstructured surface wherein in one aspect, the microstructured surface is arranged hierarchically with dual-functioning textured features. The surface may achieve adhesive properties by varying the parameters of the microstructure features. Additionally, the surface may achieve cellular and/or tissues in-growth functionality by varying the same parameters. Generally, the dual-functional aspect includes at least one surface feature having a varied periodicity which may be imposed on at least one other surface feature.

8 Claims, 17 Drawing Sheets

(56) References Cited

U.S. PATENT DOCUMENTS

| | | |
|---|---|---|
| 10,458,053 B2 | 10/2019 | Hulseman et al. |
| 10,575,667 B2 | 3/2020 | Hulseman et al. |
| 10,687,642 B2 | 6/2020 | Hulseman et al. |
| 10,889,005 B2 | 1/2021 | Hulseman et al. |
| 2002/0045907 A1 | 4/2002 | Sherman et al. |
| 2009/0069904 A1* | 3/2009 | Picha ................... A61L 27/14 623/23.72 |
| 2010/0226943 A1* | 9/2010 | Brennan ............... B08B 17/06 424/400 |
| 2011/0021965 A1* | 1/2011 | Karp ..................... A61L 15/64 602/54 |
| 2012/0052241 A1* | 3/2012 | King ..................... B08B 17/06 264/293 |
| 2013/0059113 A1* | 3/2013 | Hatton .................. B08B 17/06 428/116 |
| 2013/0268063 A1* | 10/2013 | Firstenberg ............. A61F 2/07 623/1.46 |
| 2014/0200679 A1* | 7/2014 | Bluecher ............... A61L 31/14 623/23.74 |
| 2015/0368838 A1 | 12/2015 | Hulseman et al. |
| 2017/0014111 A1 | 1/2017 | Hulseman et al. |
| 2017/0095242 A1* | 4/2017 | Milbocker ........ A61B 17/0218 |
| 2019/0062155 A1 | 2/2019 | Hulseman et al. |
| 2020/0338808 A1 | 10/2020 | Hulseman et al. |
| 2021/0086371 A1 | 3/2021 | Hulseman et al. |

FOREIGN PATENT DOCUMENTS

| | | |
|---|---|---|
| WO | 2013003373 A1 | 1/2013 |
| WO | 2013112378 A3 | 10/2013 |

* cited by examiner

MULTIFUNCTIONAL TEXTURED DEVICE

CROSS-REFERENCES TO RELATED APPLICATIONS

This application claims benefit of the following patent application(s) which is/are hereby incorporated by reference: 62/770,575 filed on Nov. 21, 2018.

A portion of the disclosure of this patent document contains material that is subject to copyright protection. The copyright owner has no objection to the reproduction of the patent document or the patent disclosure, as it appears in the U.S. Patent and Trademark Office patent file or records, but otherwise reserves all copyright rights whatsoever.

STATEMENT REGARDING FEDERALLY SPONSORED RESEARCH OR DEVELOPMENT

Not Applicable

REFERENCE TO SEQUENCE LISTING OR COMPUTER PROGRAM LISTING APPENDIX

Not Applicable

BACKGROUND OF THE INVENTION

The present invention relates generally to a microstructured device which exhibits multiple functionalities.

More particularly, this invention pertains to devices having a surface with microstructured patterns which may exhibit at least dual functionalities based on the spatial periodicity of the microstructure features.

The wettability of an implant surface can play an important role not only regarding protein adsorption but also regarding cell attachment and spreading. These physicochemical properties of the implant may influence cellular behavior near the implant through: (1) effects on the adsorption of proteins, the more non-wettable (low surface energy, higher hydrophobicity) a surface, the reduced amount of proteins on the material surface, and the strength of adhesion between protein molecules may be reduced as well; and (2) alteration of the conformation of adsorbed proteins can result from differences in the molecular topology contacting the material surface. The conformational changes can lead to differences in the expression of ligand sites interacting with cellular receptors.

A clean surface may often have a high surface free energy, while a contaminated surface may often have a lower surface energy. When a surface is not clean, then the surface can be modified by proteins and amino acids. Presence of a film on the surface most likely prevents implant integration to occur at the implant-tissue interface in vivo. Even procedures meant to clean a surface can contaminate a surface.

The sterilization of implant surfaces by steam autoclaving causes surface alteration and contamination. This may also result in a reduction of fibroblast cell attachment and spreading in vitro. However, if the surface has a high surface energy, contamination due to ionizing or heat sterilization of surface contaminants can be washed off. For example, a high surface energy texture rinsed in amino-alcohol can be decontaminated after sterilization by rinsing in citric acid followed by rinsing with physiologic saline. A flat hydrophobic surface (polypropylene) stains brightly for amine functionality after autoclaving or gamma sterilization. Such a surface would not register as pyrogenic, the current standard for assessing post-sterilization toxicity.

Epithelial cells and fibroblasts have different affinities for adhesive proteins of the extracellular matrix. It is known that in vitro, a fibronectin coating may enhance fibroblast attachment to smooth plasma-activated implant surfaces two- to three-fold, but may not promote epithelial cell attachment. In contrast, coating surfaces with laminin-1, a component of epithelial cell basement membranes, resulted in three- to four-fold enhancement of epithelial cell binding but was less effect on fibroblast attachment. Thus, the surface of an implant can play a crucial role in promoting or limiting adherence to the surface or an implant generally.

Surface topography of implant surfaces can be assessed using a confocal laser scanning profilometer. The biological functionality of a surface's topography is defined in terms of form, waviness, and roughness, with the waviness and roughness often presented together under the term "texture." The form relates to the largest structure (profile) while the roughness describes the smallest irregularities in the surface.

One problem in the prior art is the use of parameters based on averages (statistically defined) that separate surfaces with markedly different distributions of feature size. These parameters based on averages may incorrectly yield similar average values of surface roughness at each hierarchical level. Moreover, fine roughness features that may be important for performance in a given application may not contribute significantly to the calculated overall roughness value if much larger features are also present.

Therefore, there is a need for an implant surface texture which creates an immediate Wenzel-Cassie adhesion that immobilizes an implant and with a surface texture that promotes healthy integration of the implant with the surrounding tissue.

BRIEF SUMMARY

In one embodiment, a microstructured surface may include a substrate having at least a first hierarchical microstructure. The microstructure may include a plurality of microstructure features which may include one or more parameters that progressively vary in a spatial periodicity across the substrate.

In one embodiment, the microstructured surface may include one or more parameters that are selected from the group comprising height, width, diameter, shape, and pitch, and combinations thereof.

In one embodiment, the microstructured surface may further include the plurality of microstructure features having at least a first set of microstructure features and second set of microstructure features. The at least first set of microstructure features may be disposed about the substrate, and the at least second set of microstructure features may be smaller than the at least first set of microstructure features and may be disposed on the at least first set of microstructure features.

In one embodiment, the microstructured surface may include the substrate being flat and the at least first set of microstructure features may be disposed about the flat substrate in a uniformly spaced square array.

In one embodiment, the microstructured surface may include the substrate being configured to exhibit a sinusoidal pattern with a height of between 50 to 500 microns.

In one embodiment, the microstructured surface may include at least one of the first and second set of microstructure features having a width that varies periodically across the substrate.

In one embodiment, the microstructured surface may include at least one of the first and second set of microstructure features having a cross sectional profile that varies periodically from circular to oval across the substrate.

In one embodiment, the microstructured surface may include at least one of the first and second set of microstructure features having a height that varies periodically across the substrate.

In one embodiment, the microstructured surface may include a periodically varying height of the at least first microstructure features which may be configured to produce a pyramidal structure.

In one embodiment, the microstructured surface may include at least one of the first and second set of microstructure features having a pitch that varies periodically across the substrate.

In some embodiment, the microstructured surface may include a periodically varying pitch of the at least first microstructure features being configured to produce a structure chosen from the list comprising concave, convex, v-saddle, and h-saddle, and combinations thereof.

In one embodiment, a microstructured surface may include a surface that includes at least a first hierarchical microstructure comprising a plurality of microstructure features. The plurality of microstructure features may include one or more parameters that vary in a spatial periodicity and configured to produce at least one of a Wenzel surface or a Cassie surface, or a combination Wenzel-Cassie surface.

In one embodiment, the microstructured surface may include one or more parameters that may be selected from the group comprising height, width, diameter, shape, and pitch, and combinations thereof.

In one embodiment, the microstructured surface may include a plurality of microstructure features including at least a first set of microstructure features and second set of microstructure features. The at least first set of microstructure features may be disposed about the substrate, the at least second set of microstructure features may be smaller than the at least first set of microstructure features and may be disposed on the at least first set of microstructure features.

In one embodiment, the microstructured surface may include a substrate that is flat and the at least first set of microstructure features may be disposed about the flat substrate in a uniformly spaced square array.

In one embodiment, the microstructured surface may include the substrate being configured to exhibit a sinusoidal pattern with a height of between 50 to 500 microns.

In one embodiment, the microstructured surface may include the at least first and second set of microstructure features being configured to produce an area excluding solutes from a volume of water.

In one embodiment, the microstructured surface may include at least one of the first and second set of microstructure features having a cross sectional profile that varies periodically from circular to rectangular across the substrate.

In one embodiment, the microstructured surface may include a hole that is disposed in the substrate between a first and a second feature of the at least first set of microstructure features, the hole being configured to produce a capillary effect.

In one embodiment, the microstructured surface may include a substrate having a flat surface. The at least first set of microstructure features may include ridges in a uniformly spaced array, the at least second set of microstructure features may include a plurality of cylinders disposed about a top portion of the ridges, and further may include a third set of microstructure features disposed about an interstitial area between the plurality of cylinders including a second plurality of cylinders.

To enable the objectives, technical contents, characteristics and accomplishments of the present invention to be more easily understood, the embodiments of the present invention are described in detail in cooperation with the attached drawings below.

DETAILED DESCRIPTION

Figure 1:
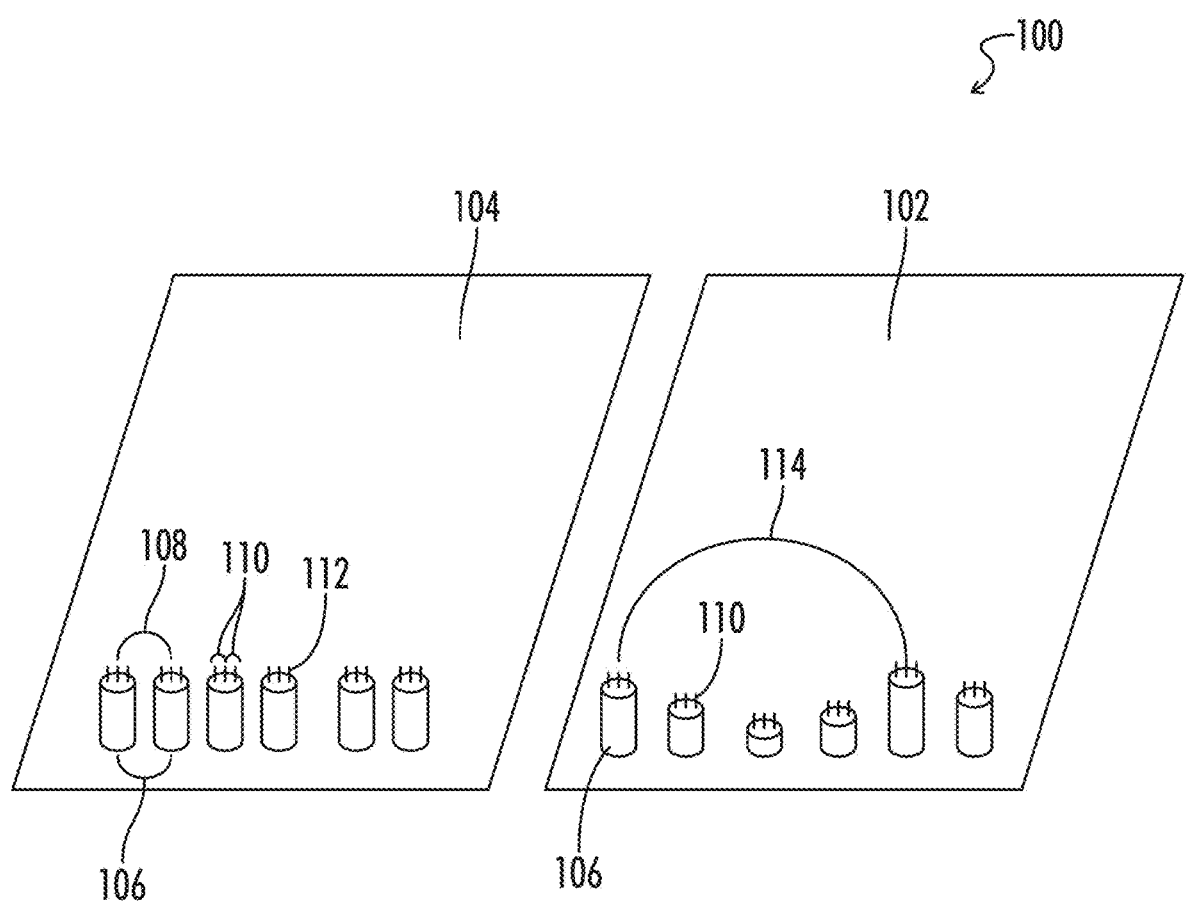
FIG. 1 is an embodiment of dual-functional hierarchical surfaces to single-functional hierarchical surfaces.

The following detailed description and appended drawings describe and illustrate various embodiments of the current disclosure. The description and drawings serve to enable one skilled in the art to make and use the invention. Although the present disclosure describes various embodiments, those skilled in the art will recognize that changes may be made in form and detail without departing from the spirit and scope of the invention. As such, it is intended that the following detailed description be regarded as illustrative rather than limiting, and that it is the appended claims, including all equivalents thereof, which are intended to define the scope of the invention.

In the present application, the terms "comprise(s)," "include(s)," "having," "has," "contain(s)," and variants thereof, are intended to be open-ended transitional phrases, terms, or words that do not preclude the possibility of additional acts or structure.

As used herein, the term "microscopic" refers to features of small enough dimension so as to require an optic aid to the naked eye when viewed from any plane of view to determine its shape. One criterion is found in Modem Optic Engineering by W. J. Smith, McGraw-Hill, 1966, pages 104-105 whereby visual acuity, " . . . is defined and measured in terms of the angular size of the smallest character that can be recognized." Normal visual acuity is considered to be when the smallest recognizable letter subtends an angular height of 5 minutes of arc on the retina. At a typical working distance of 250 mm (10 inches), this yields a lateral dimension of 0.36 mm (0.0145 inch) for this object.

As used herein, the term "microstructure" means the configuration of features wherein at least 2 dimensions of the features are microscopic. The topical and/or cross-sectional view of the features must be microscopic. The function of the pressure sensitive adhesive article is critically dependent on the form of the microstructure, which may consist of positive and negative features.

As used herein, the term "microstructure feature" means an individual feature, or group of features projecting out of a surface with a specific range of sizes. For example, a microstructure feature may include a single pillar or a group of pillars with radius 10-20 microns and height 30-40 microns, which is distinguished from another dimensional feature of pillars with radius 80-100 microns and height 80-125 microns. Generally, the volumes of microstructure features are different by a factor of 10 or more. The spatial periodicity of the microstructure features occurs over a segment or portion of the substrate surface. The spatial periodicity occurs gradually, or progressively, across the surface and can occur in all three-dimensions, either individually or simultaneously.

As used herein, the term "positive features" means features projecting out of the microstructured molding tool, microstructured liner, microstructured backing, or microstructured pressure-sensitive adhesive layer.

As used herein, the term "negative features" means features projecting into the microstructured molding tool, microstructured liner, microstructured backing, or microstructured pressure-sensitive adhesive layer.

As used herein, the term "suctional aspect" is a negative feature capable of generating capillary rise.

As used herein, the term "embossable" refers to the ability of a substrate layer to have part of its surface raised in relief, and other parts of its surface lowered in relief, especially by mechanical means.

As used herein, the term "substrate layer" refers to a piece of a substance such as thermoplastic, or polymer that can receive microstructures by embossment, molding, printing, and casting, where the microstructures become integral to the substrate layer.

As used herein, the term "wetting" means spreading out over and contacting a surface with a fluid. Aqueous fluids on hydrophilic surfaces are wetting.

As used herein, the term "dewetting" means a fluid contracting from contact with a surface. Aqueous fluids on hydrophobic surfaces are dewetting.

As used herein, the term "repositionable adhesives" refers to those adhesive microstructured surfaces which upon application to a specific target substrate can be removed without causing damage to the substrate, without leaving residue on the substrate, and without causing damage to the backing or liner over a range of peel forces.

As used herein, the term "multi-functional microstructure" refers to liquid, solid, and gas domains that develop on a microstructured surface when the surface comes into contact with a target surface. These domains lower the surface energy of the microstructured surface and the target surface at the interface between the two surfaces. The interface is rendered adhesive by the formation of a lower energy interface which requires energy to be supplied to the interface in order to separate the two surfaces. The physical forces responsible for domain formation include van der Waals forces, Casimir forces arising from quantum interactions with the zero-point field, intermolecular forces, London dispersion forces, Debye force, Keesom forces, and hydrogen bonding. Adhesive microstructure does not refer to any chemically reactive substance applied to a surface to make it grip a target surface.

As used herein, the term "permanently repositionable multi-functional microstructured surface" refers to repositionable microstructured surface for which the strength of adhesion to a given target substrate does not change substantially with time under application conditions.

As used herein, the term "temporarily repositionable multi-functional microstructured surface" refers to those repositionable microstructured surfaces which build adhesion with time, pressure, or temperature. This phenomenon is sometimes referred to as a "suction effect" wherein the interface between the microstructured adhesive and target surface progressively thins and increases the energy of disassociation.

As used herein, the term "energy of dissociation" refers to the difference in the surface energies of the microstructure and target surfaces apart and joined in an interface. Energy of dissociation is a quantitative measure of the degree of adhesion.

As used herein, the term "target substrate" refers to a surface to which the pressure-sensitive microstructured adhesive is applied for an intended purpose.

As used herein, the term "exclusion zone" refers to a region between a surface and water wherein due to the hydrophilicity of the surface, either due to surface texture or chemical characteristics, water thermodynamically excludes ions and molecules that are not water.

As used herein, the term "structured water" refers to a state of water wherein the water molecules in solution take a transition hexagonal form, which is reinforced and sustained by the surface energy and chemistry between water and a solid surface.

As used herein, the term "capillary action" (sometimes capillarity, capillary motion, capillary rise, capillary effect, or wicking) is the ability of a liquid to flow in narrow spaces without the assistance of, or even in opposition to, external forces like gravity. The effect can be seen in the drawing up of liquids between the hair of a paintbrush, in a thin tube, in porous materials such as paper and plaster, in some non-porous materials such as sand and liquefied carbon fiber, or in a cell. It occurs because of intermolecular forces between the liquid and surrounding solid surfaces. If the diameter of the tube is sufficiently small, then the combination of surface tension and adhesive forces between the liquid and container wall act to propel the liquid.

As used herein, the term "pitch" refers to the center-to-center distance between two microstructures in a particular direction. If the direction is not specified, then the pitch is assumed to be equal in at least two orthogonal directions.

As used herein, the term "friction" refers to the conventional interaction of one surface texture upon another, wherein deformations between the surfaces, direct physical contact, and the resistance to translation across non flat surfaces is inhibited. These are direct structure on structure interference, where the structure on one surface is a solid-to-solid interaction with the other surface which prevents translation. Those that teach frictional effects as an adhesive functionality do not teach the objects of the present application.

The present disclosure discusses the balancing of a two-dimensional interface (immersed in three dimensions) between the two-dimensional non-slip implant/tissue surface and the three-dimensional needs of a tissue scaffold. The dual functional aspect mimics the true three-dimensional world in which individual cells live. Cells travelling interstitially travel along planar structures which mimic surfaces that are folded, curved, or stretched out. This three-dimensional aspect is presented to the cell on a two-dimensional surface.

A substrate's surface can be composed of sums of sinusoidal gratings or of circular dots, and may be designed to differentiate between orientation and frequency information present in perspective images of the surfaces. Cellular perception of concavities, convexities, saddles, and slants can arise from signature patterns of orientation modulations. These oriented modulations can be thought of as the temporal frequency modulation of a fixed spatial frequency that a cell may experience as it travels across the two-dimensional implant surface.

The use of a tissue scaffold to illustrate the dual functionality of a microstructured surface is not meant to be limiting. For example, the microstructure of a fingertip surface, which is three-dimensional on a micro-scale can mimic cellular interaction, whereas the macroscopic surface of the fingertip surface is globally two-dimensional. A wet interface between a fingertip and a surface disclosed herein establishes a Wenzel-Cassie grip with the finger tissue macroscopically by inducing ripples in the fingertip tissue. And further establishes a second level of Wenzel-Cassie adhesion with the pre-existing fingerprint structure. Generally, there may be multiple adhesion mechanisms not described by classical friction that include Wenzel-Cassie zones, surface induced eigen wrinkle modes, capillary and suctional aspects, and Schallamach waves.

By modulating a surface pattern for tissue in-growth where the individual surface features to be modulated are themselves hierarchical features, unexpected benefits are obtained. For example, in some embodiments, small pillars may be placed on top of larger pillars in an hierarchical arrangement, wherein one aspect is relatively more hydrophobic at a molecular scale and resists contamination. On the other hand, cells are less affected by this smaller scale hydrophobicity and respond to the modulated pattern.

Modulation as herein used describes the periodic or random changing of features on a characteristic scale. For example, in some embodiments, five-micron tall pillars may be modulated in their diameter sinusoidally from a minimum to a maximum. Generally, features useful in modulation designs may involve dimensions, geometry, and pitch or spacing. In the case of modulating a feature geometry, the cross section of pillars may vary in a continuous fashion from a circular cross section to an elliptical cross section.

Functional duality may occur when complex surfaces are prepared using random processes. A more sophisticated, albeit computationally intensive approach is the use of Fourier transforms to fit observed profiles of surfaces and enable roughness in different size ranges, termed windows, to be determined and correlated with biological responses. For these reasons, optimal biological functionality is achieved when the various texture levels are defined by distinct periodicities on distinct scales. Many of these periodicities are not readily observed by the human eye, or recognized as distinct by human perception, but nevertheless are strongly sensed by cells. Textures designed to engage macroscopic features of animal tissue, e.g., muscle fibers, enclosing layers, tendons, vessels and the like, do not engage microscopic cells, particularly those cells which are nomadic within the stationary structures of the body.

Surface roughness can occur in two principal planes: one perpendicular (transverse) to the surface and one in the plane of the surface (longitudinal). A wave can be transverse, where a pattern is an oscillation that is perpendicular to the propagation of energy transfer (by cells), or longitudinal: the pattern is an oscillation parallel to the direction of energy propagation. The orientation of the irregularities may be either isotropic or anisotropic. Surface structures without a dominant direction may be considered isotropic.

In some embodiments, these surfaces may be incorporated into a tissue scaffold implant. The composition and orientation of the protein film and the orientation of the molecules that are adsorbed on the implant surface may be affected by the surface roughness.

Surface texture may affect cell propagation. The wettability of smooth titanium surfaces may be correlated to fibrin adsorption but does not exist on rough titanium. Epithelial cells may attach and spread more readily on polished and etched surfaces than on rougher surfaces (sandblasted).

In comparison to a smooth surface, a rough surface may promote the formation of multiple filopodia at the periphery of immortalized epithelial cells, while the cells were round and in direct contact with each other on more smooth surfaces. It may be assumed that the presence of filopodia suggests a higher level of adhesion. This assumption is incorrect. It is not a normal behavior for epithelial cells to display filopodia. The epithelial cells actually may not be in direct contact with the valleys of the roughened titanium, but rather bridge over the valleys.

An isotropic surface texture may influence growth and proliferation of cells, leading to contact guidance, which depends upon the micro-pattern and size of the different geometrical elements. Contact guidance refers to the tendency of cell locomotion to be guided or directed by the dominating direction of the surface topography of the substratum to which the cells are adhering. Circumferential grooves on surfaces may guide fibroblasts to form oriented capsule-like structures, whereas cells grown on porous surfaces may show no preferred orientation. Thus, there may be a hierarchy in cell response to features, with larger features dominating smaller ones.

Figure 1A:
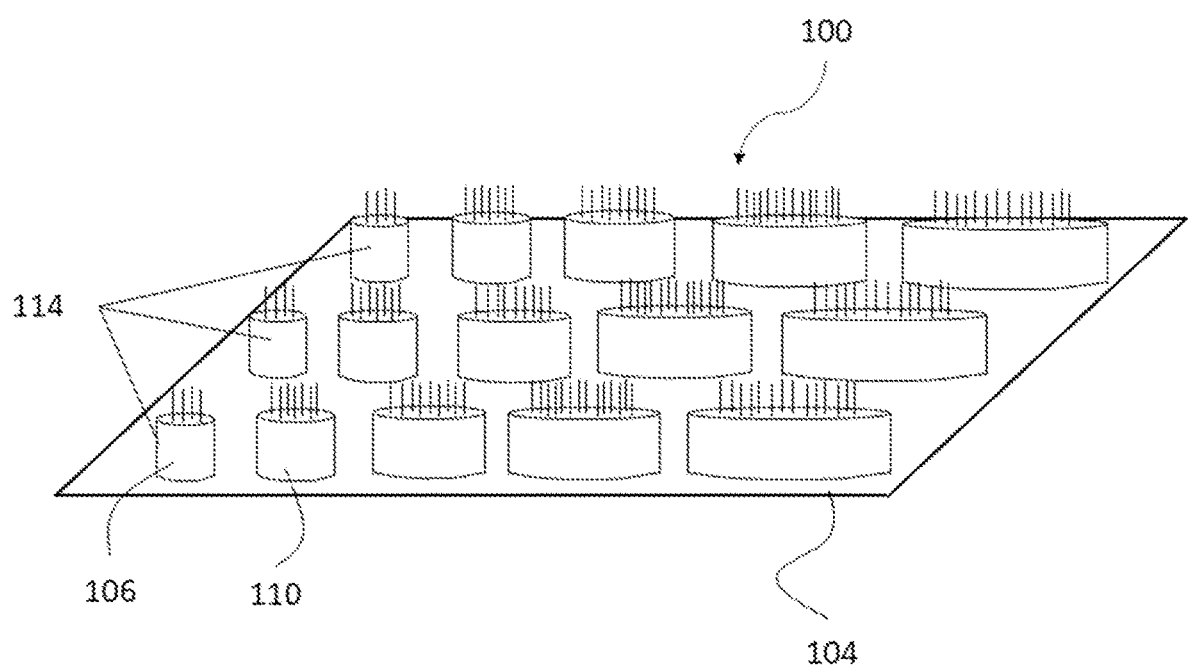
FIG. 1A is an embodiment of a dual-functional hierarchical surface including a set of microstructure features having a cross-sectional profile that varies periodically from circular to oval across the substrate.

The relationship between surface textural configuration and the shape that cells assume when cultured on it specifically elongation, may be determined by the surface texture. Moreover, cells can be sensitive to feature size. Features as small as 0.2 microns have been observed to produce a cell response Referring now to FIGS. 1 and 1A, 100 compares dual-functional hierarchical surface 102 to single-functional hierarchical 104 surface. The hierarchical structure of surface 104 may be formed by a first periodic structure 106 of one frequency 108 and a second periodic structure 110 of another frequency 112. Dual-functional hierarchical surface 102 may include a dual periodic structure 114 comprising the same elements 106 and 110.

Figure 2:
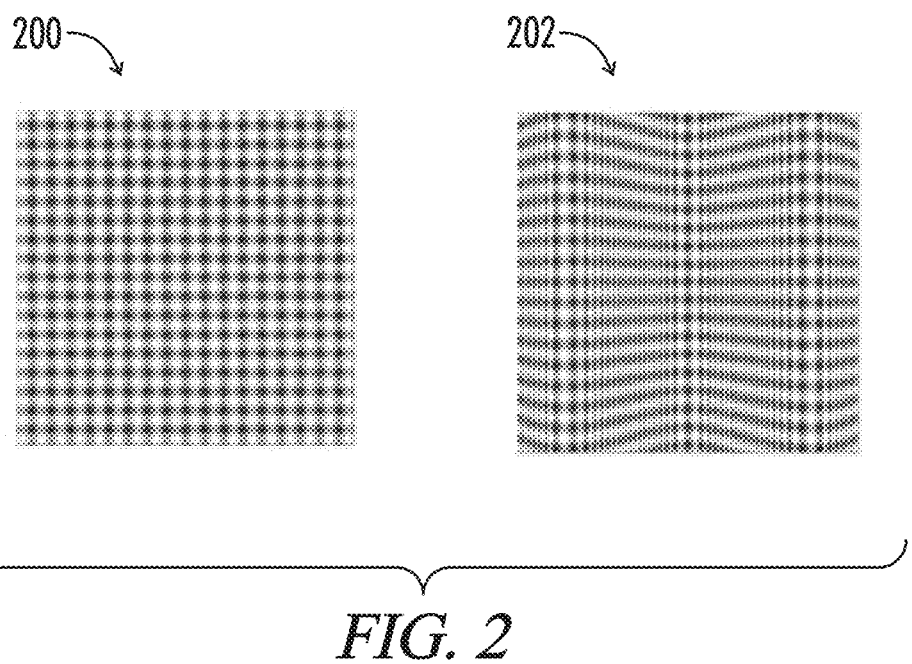
FIG. 2 is an embodiment of a square spatial frequency grid, and the same grid modified by orientation modulation.

Referring to FIG. 2, a square spatial frequency grid 200 under the same grid modified by orientation modulation 202, appears as a three-dimensional tissue scaffold. Note, both 200 and 202 may actually be flat two-dimensional surface textures. The interface between implant and tissue may be two-dimensional, and the interface between a mobile cell and the implant may be pseudo-three dimensional. When a pattern presents a folded appearance, as in 202, the actual frequency/pillar size on the pseudo-surface may remain unchanged, but texture distortions may occur on the implant surface by varying pillar size and spacing such that the ratio may be a constant.

Figure 3:
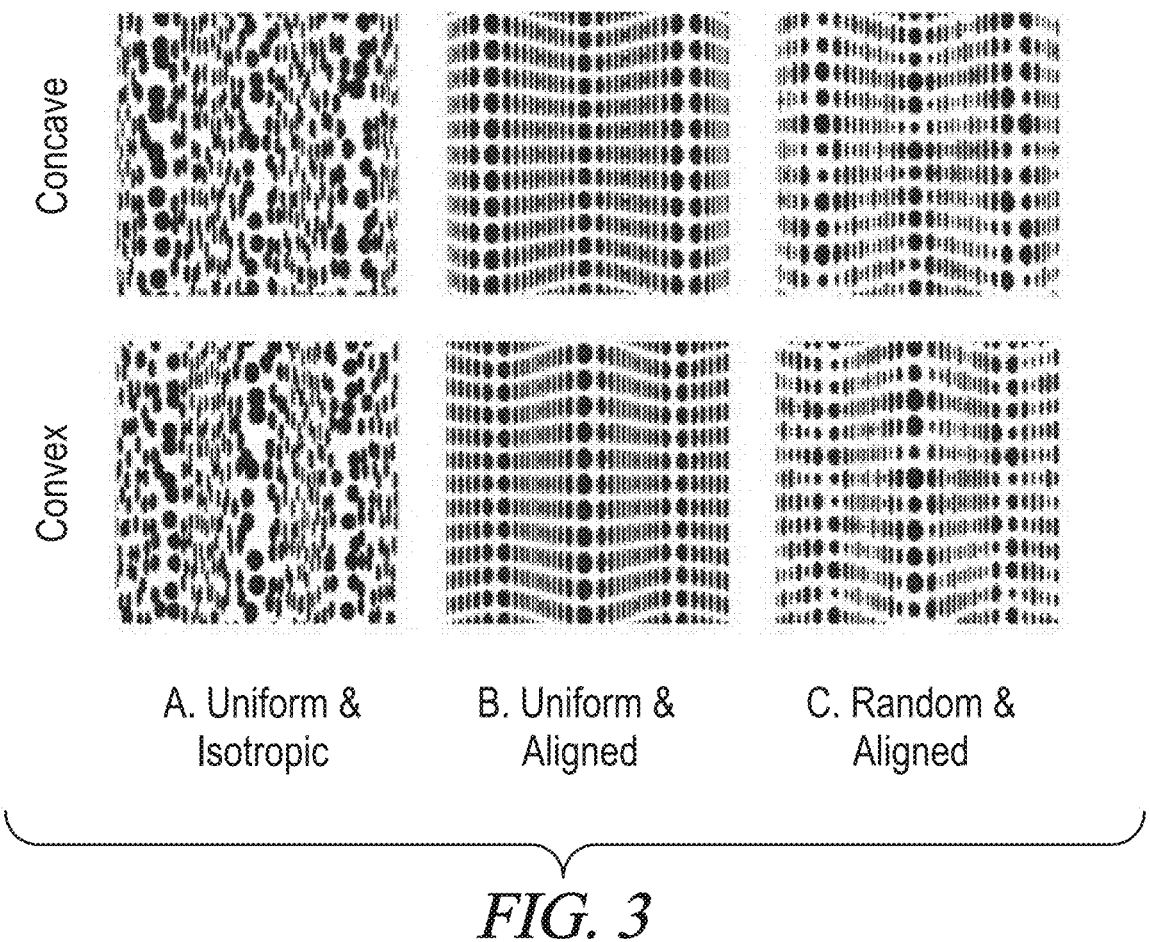
FIG. 3 is an embodiment of an orientation modulation of a square grid of uniform diameter and uniformly center-spaced pillars.

Referring to FIG. 3, various embodiments are illustrated which depict orientation modulation of a square grid of uniform diameter and uniformly center-spaced pillars. The top row of FIG. 3 illustrates concave-centered patterns, while the bottom row illustrates convex-centered patterns. The first column may include uniform diameter pillars randomly distributed. The second column may include uniform diameter pillars which may be aligned. The third column may include random diameter pillars which may be aligned.

Figure 4:
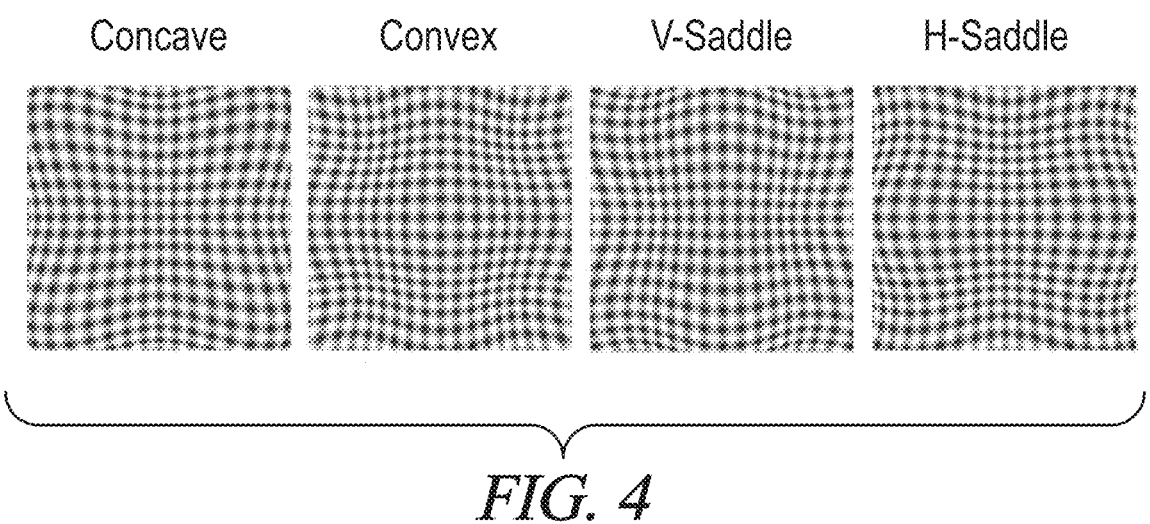
FIG. 4 is an illustration of different forms of pseudo-deformation.

Referring to FIG. 4, various embodiments are illustrated with different forms of pseudo-deformation.

Figure 5:
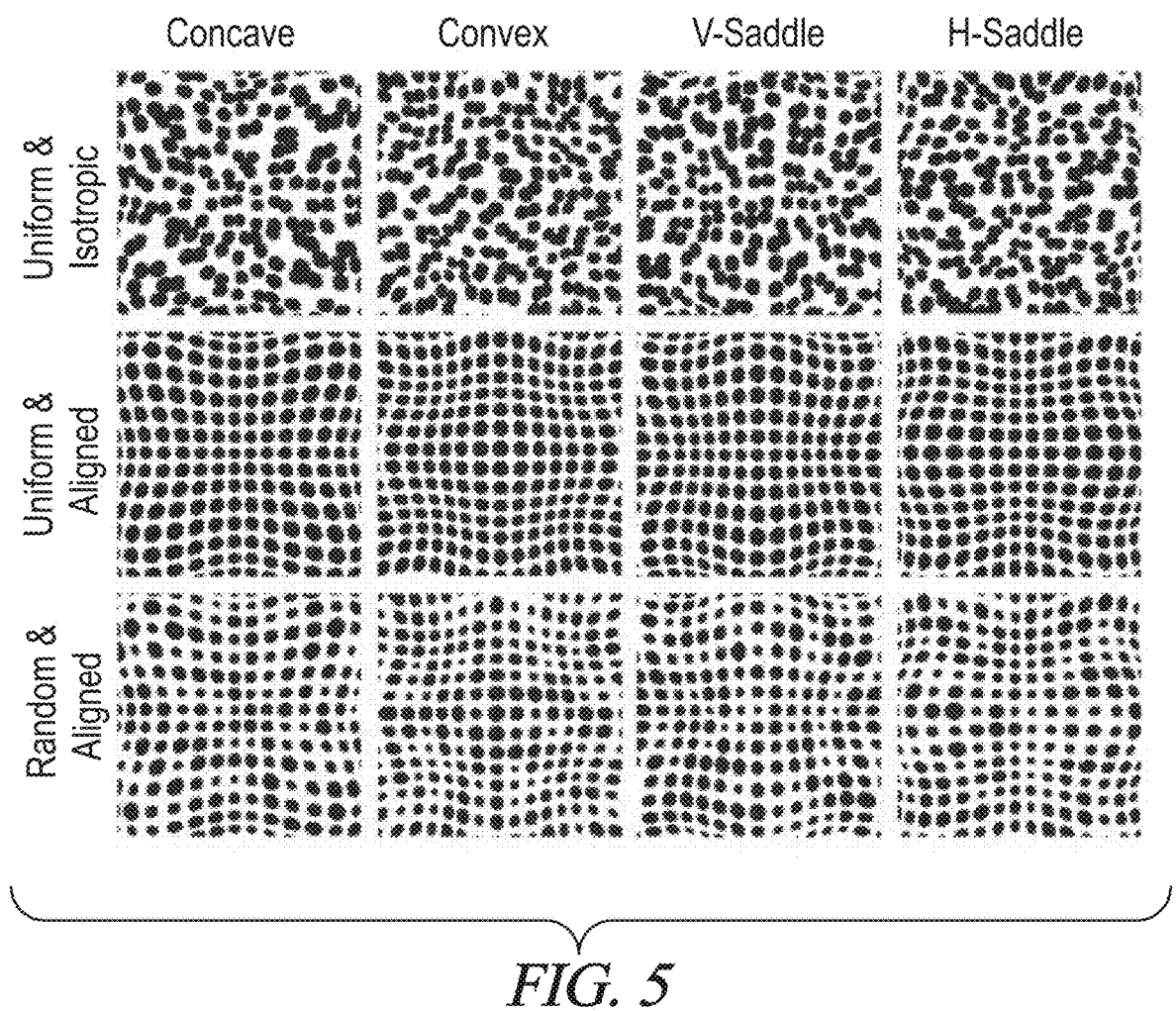
FIG. 5 is an illustration of four types of pseudo-surfaces (columns).

Referring to FIG. 5, some embodiments are illustrated wherein a square grid of pillars with various orientation modulations are represented. The examples of FIG. 5 may describe the four types of pseudo-surfaces (columns), each type differing in the types and distribution of cells, and hence the structure and composition of the eventual ingrowth tissue. FIGS. 2-5 may describe the basic frequency vocabulary of the present disclosure.

Another aspect of surface patterning which can direct cellular ingrowth but may adversely affect the implant-tissue interface immobilization and the implant durability, is localized regions of high surface tension. To satisfy these opposing constraints the notion of a pseudo-stress can be introduced, and as before this may be possible because a cell is microscopic and the tissue is macroscopic.

Patterns that may induce pseudo-stress may be a class of microscopic instability patterns. Such patterns can be an ingredient in application-oriented design as a technique for induction or modification of microscopic, periodicity-dependent structural or surface properties such as chirality (enantiomeric), wave propagation and phononic properties, modulated nano/micro patterns, hydrophobicity, or generating macroscopic responses in periodic solids.

Figure 6:
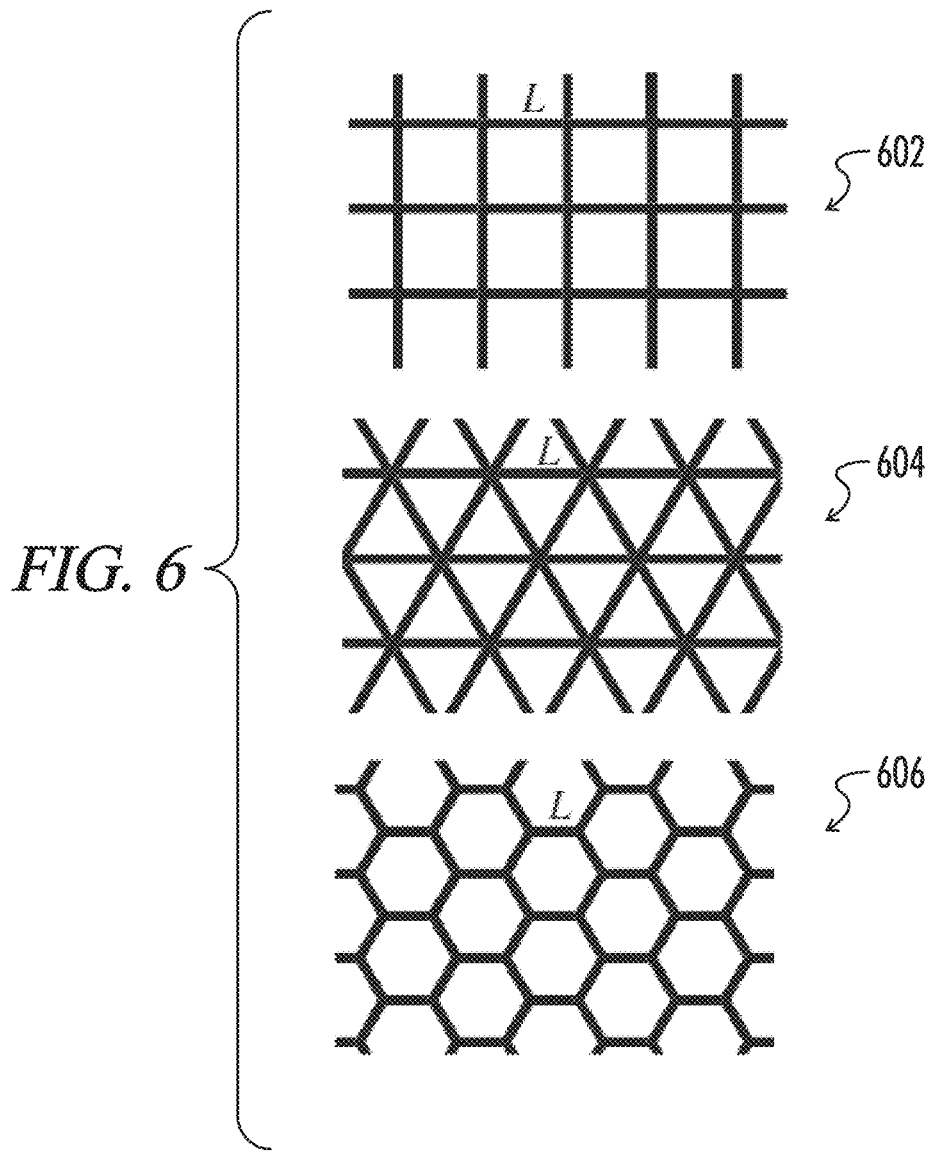
FIG. 6 is an illustration of an undeformed square grid, triangular grid, and hexagonal grid.

As illustrated in FIG. 6, deformations of undeformed rectangular lattices which may include squares 602, triangles 604, and hexagons 606 may be considered.

Figure 7:
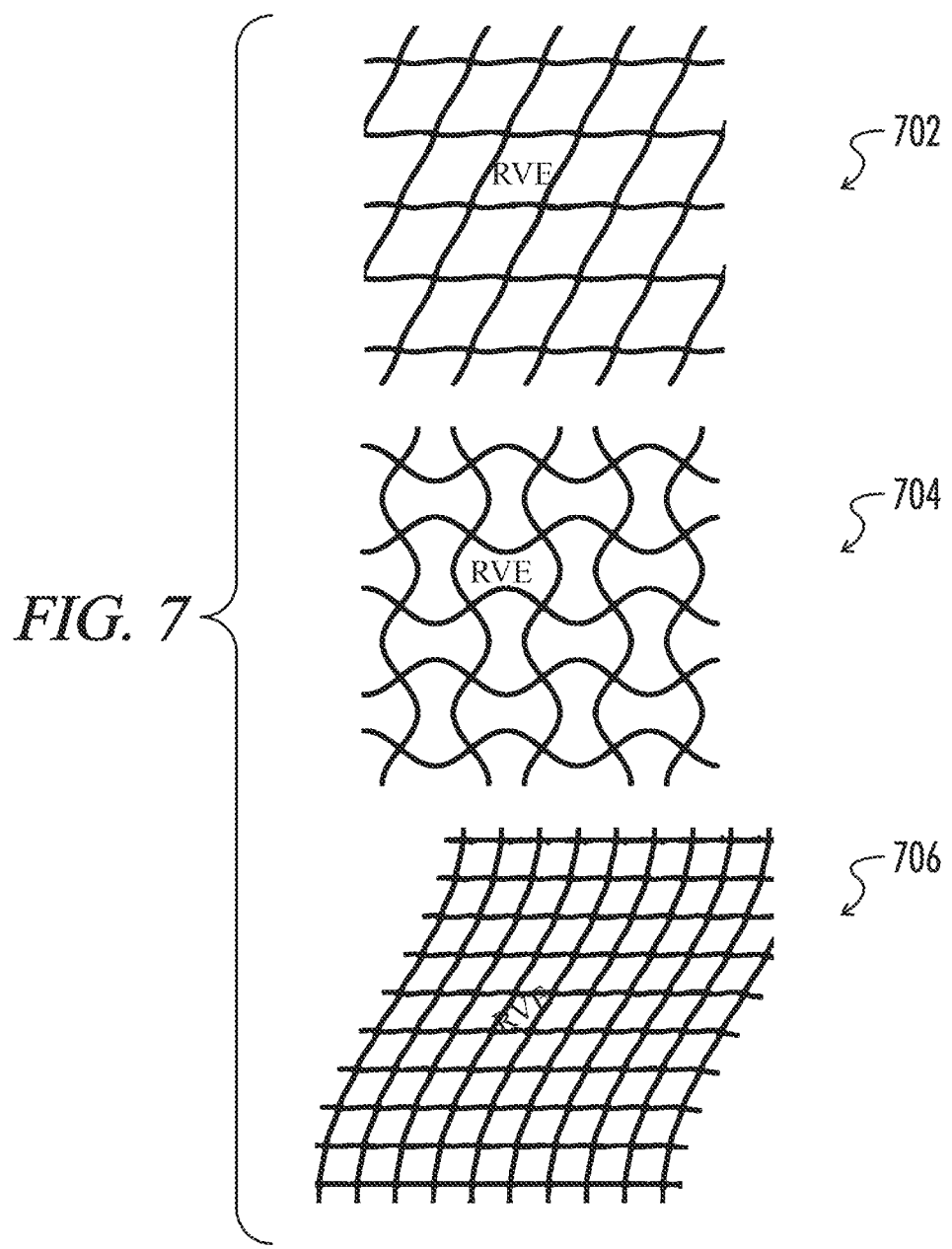
FIG. 7 is an illustration of three deformation modes including shear, compression, and periodic.

Additionally, as disclosed below, chiral forms may also be considered. There may be three deformation modes for the square lattice 602. Referring to FIG. 7, the three deformation modes 700 may include shear 702, compression 704, and periodic 706 square lattices.

Figure 8:
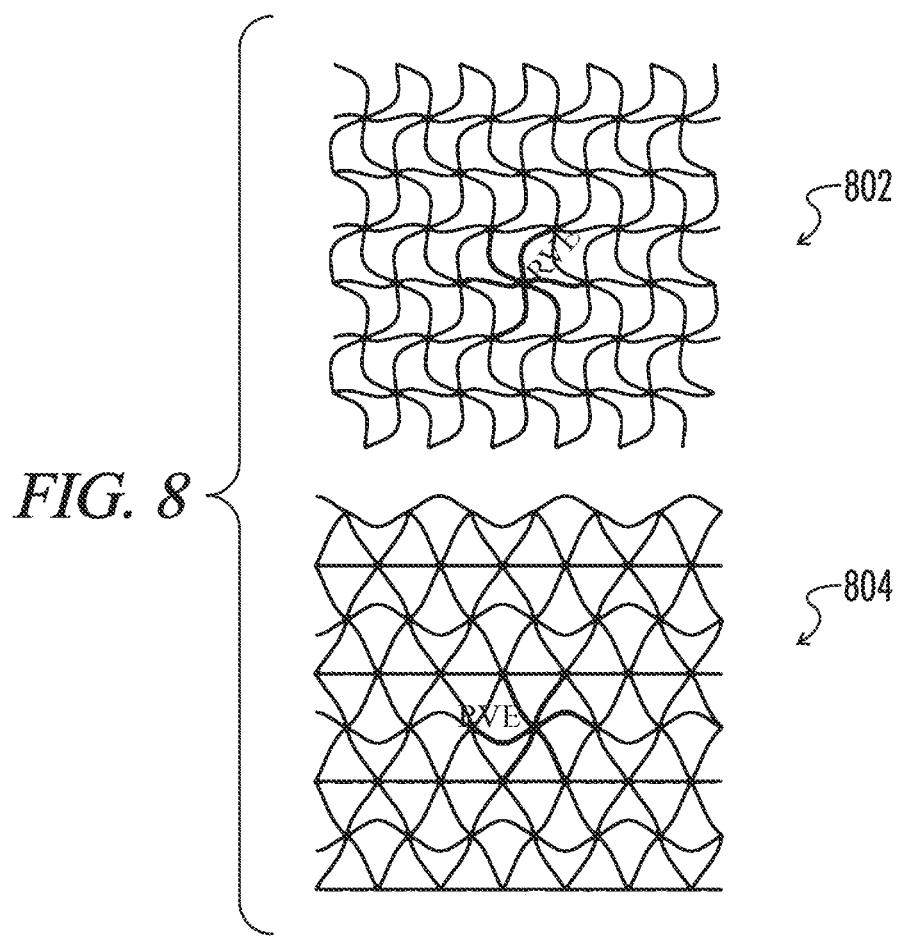
FIG. 8 is an illustration of a compression mode and a periodic mode.

Referring to FIG. 8, two additional deformation modes 800 are illustrated including a compression mode 802 and a periodic mode 804.

Figure 9:
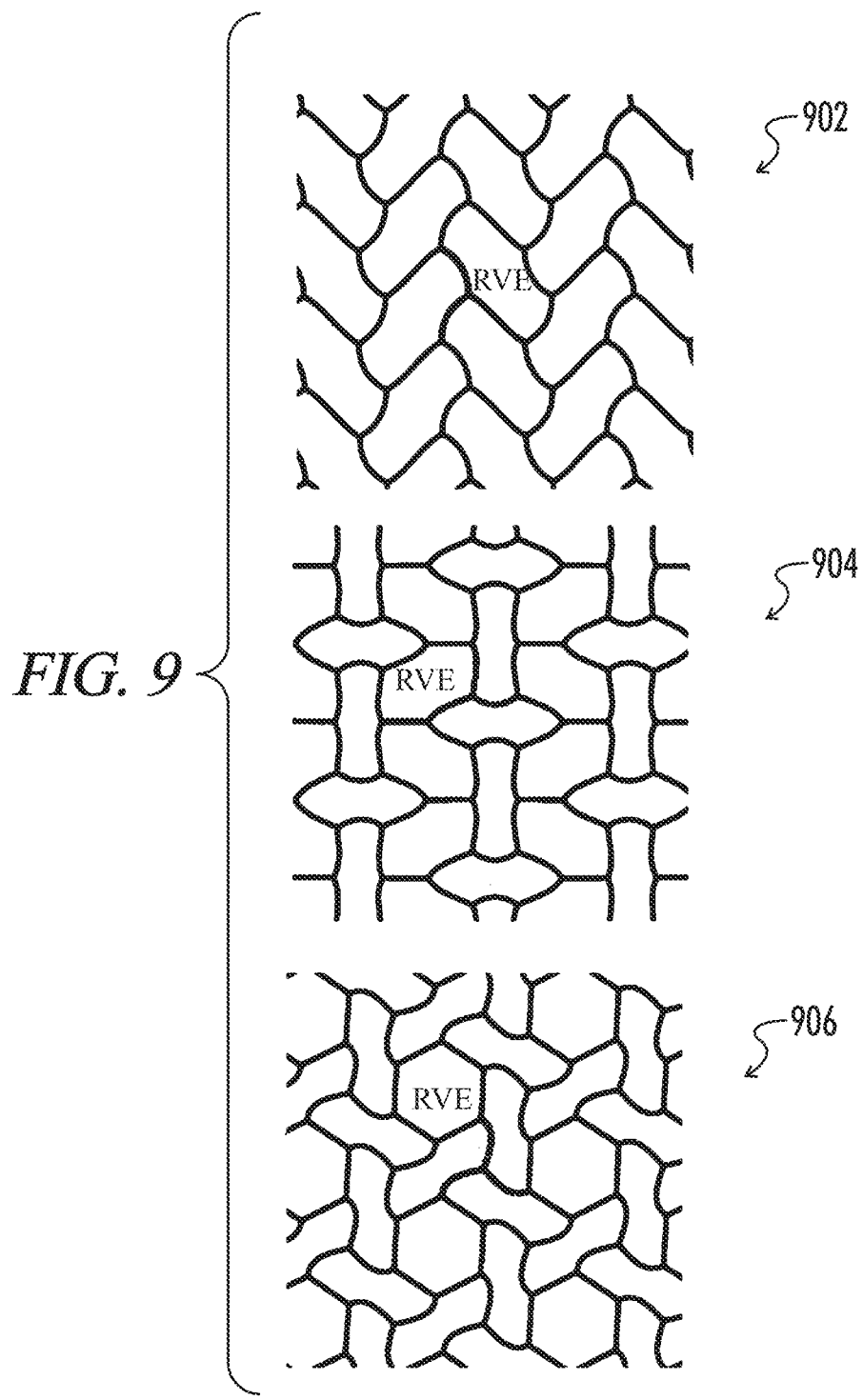
FIG. 9 is an illustration of axial compression, biaxial compression, and periodic compression.

Referring to FIG. 9, the deformation modes 900 may include axial compression 902, biaxial compression 904, and periodic compression 906.

Figure 10:
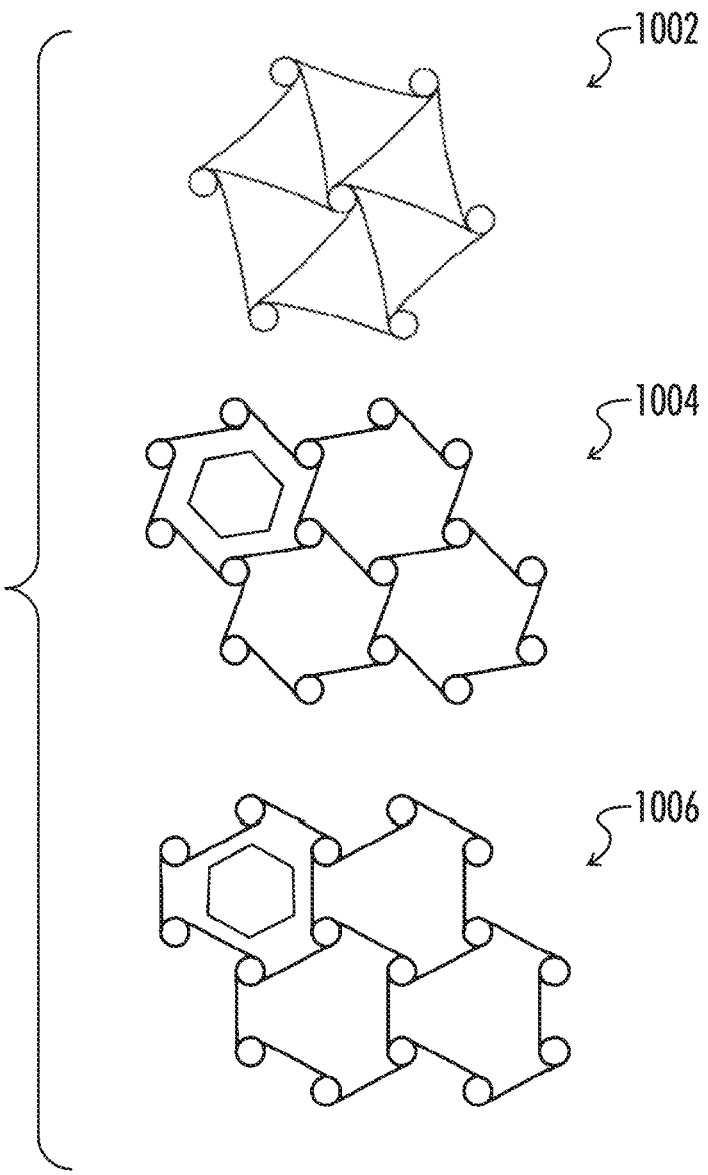
FIG. 10 is an embodiment of the chiral forms of the triangular grid and two forms of chiral hexagonal lattices.

Now, referring to FIG. 10, the chiral forms of the triangular lattice 1002 is depicted. Additionally, two other forms of chiral hexagonal lattices 1004, 1006 are depicted.

Figure 11:
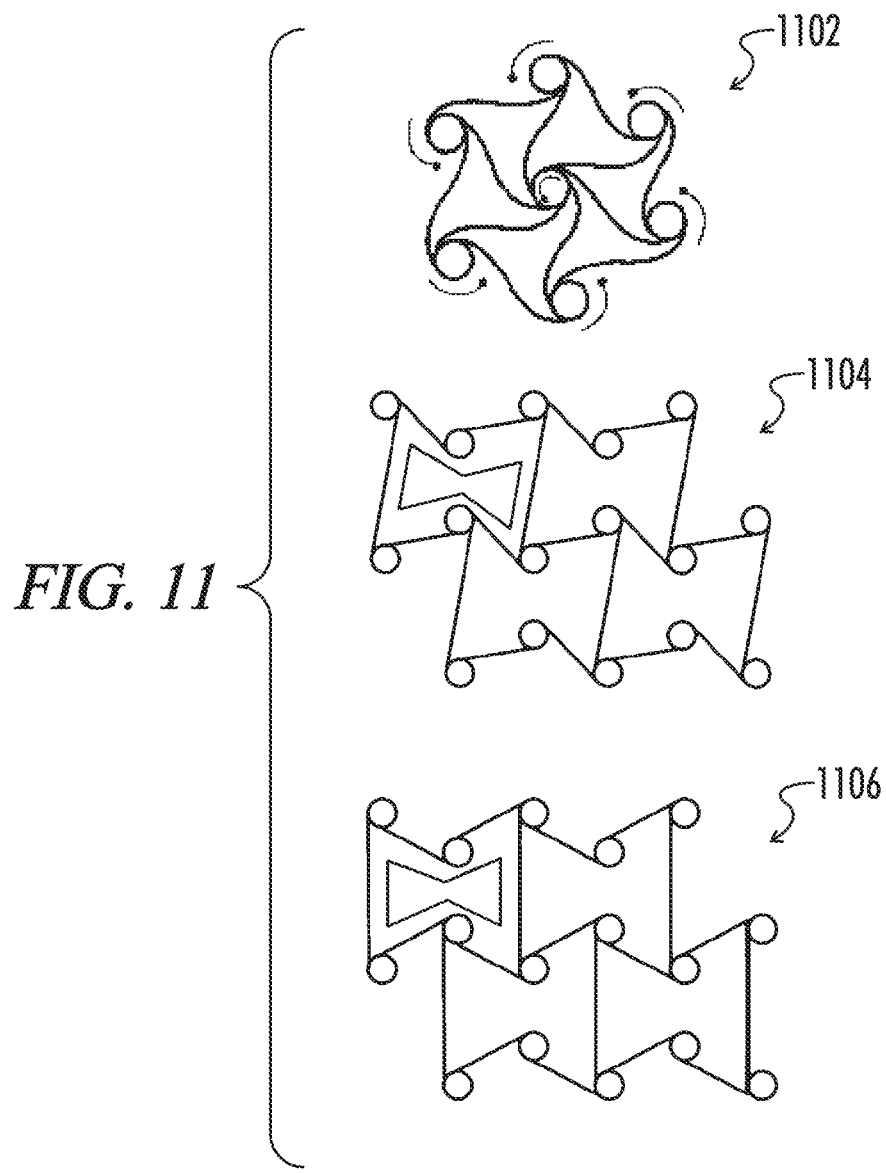
FIG. 11 is an embodiment of compressed chiral forms of a triangular grid and two forms of chiral hexagonal lattices.

Now, referring to FIG. 11, the compressed chiral triangular form 1102 and two compressed chiral hexagonal forms 1104, 1106 are illustrated. It should be noted that compressed chiral triangular lattice 1102 only depicts the left chiral form, but it will be understood by a person of skill in the art that the right chiral forms are obtained by mirror reflection (not rotation).

Figure 12:
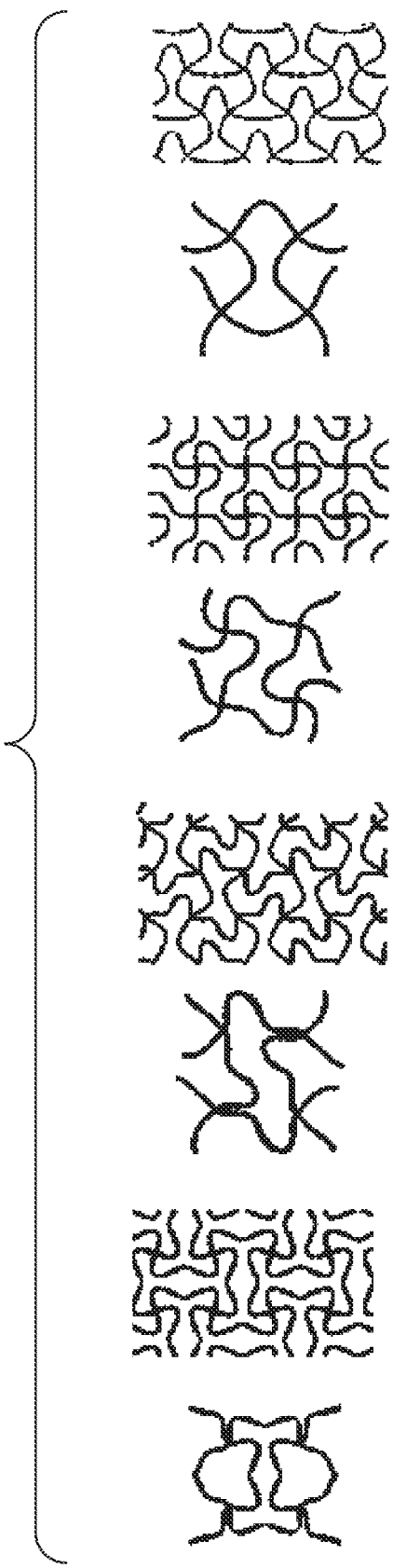
FIG. 12 is an embodiment of a wave propagation form of the square lattice and associated unit cells.

Now, referring to FIG. 12, some embodiments of wave propagation forms of the square lattice and associated unit cells are depicted. These waveforms are given by periodic translations and rotations of the nodes of a regular square lattice.

Regarding localization of an implant relative to tissue, it has been unexpectedly discovered that localization of the implant can be improved by anticipating the waveform the tissue at the tissue-implant interface might undergo before mobilization (eigenmode). For example, a medium, such as tissue, may buckle in normal modes, or eigenmodes. When a waveform of a surface pattern anticipates one of these eigenmodes, then localization relative to tissue may be enhanced. In this way, stresses between implant and tissue may increase the shear force required for implant translation relative to the tissue.

A need for an adhesive article which exhibits initial repositionability when adhered to a variety of target substrates has been identified and, through the independent variation and selection of microstructured dual patterns, the adhesive article may exhibit separate effects on at least two scales.

The present disclosure also relates to an article, including adhesive surfaces and transfer coatings, bearing a continuous adhesive layer having a microstructured surface wherein the microstructured surface may include at least two kinds of features. Further, the article may include a lateral aspect ratio of the features ranging from about 0.1 to about 10 for each feature, and at least one feature dimension may vary by at least a factor of 10%. For example, in some embodiments two sets of pillars, one 5 microns in diameter and 30 microns tall and another set of pillars at least 15 microns in diameter and at least 75 microns tall may be disposed about the surface of the article. In some embodiments, the first set of pillars may be disposed on the top surface of the second set of pillars. At least two of the feature dimensions (height, width, and diameter) must be microscopic. All three of the feature dimensions (height, width, and diameter) may be microscopic. The dual functionality of the article may be achieved by varying one or more of the parameters across the surface of the device, the variation may be spatially periodic, or within a statistical range. Similarly, the dual functionality may be achieved by varying the density of the pillars, or the pitch between one feature and an adjacent feature.

In at least one embodiment a dual-functional surface may include at least two microstructured patterns of different dimensions arranged hierarchically wherein at least one of the microstructured patterns may be modulated or the hierarchical combinations creates a modulation aspect. A modulation aspect is a patterned feature, usually periodic, that affects a contact surface at a different scale than the underlying hierarchical structure.

Some embodiments may include a dual-functional surface comprised of at least two microstructured patterns of different dimensions arranged hierarchically wherein at least one of the microstructured patterns may be dual functional or the hierarchical combinations create a dual-functional aspect. In particular, the embodiment may consist of a substrate layer onto which is embossed a two-dimensional pattern in such a way that both sides of the substrate layer may exhibit a sinusoidal aspect. Furthermore, on top of the sinusoidal substrate layer solid cylinders may be embossed filling each complete square cycle of the sinusoidal pattern with between 10 and 100 equally spaced cylinders. On top of each cylinder in the first pattern of cylinders may be 1 to 10 solid cylinders of a smaller dimension. The dual-functional effect may be initiated by modulating the first cylinder orientations with respect to a virtual flat surface. In particular, the first cylinders may be oriented perpendicular to the sinusoidal surface.

Some embodiments may include a dual-functional patterned surface comprised of three microstructured patterns of different dimensions arranged hierarchically wherein at least one of the microstructured patterns is dual-functional or the hierarchical combinations creates a dual-functional aspect. In particular, an article may consist of a flat substrate layer. On top of the flat substrate layer may be embossed solid cylinders in a uniformly space square array. On top of each cylinder in the first pattern of cylinders may be embossed 1 to 10 solid cylinders of a smaller dimension. The first cylinders may vary in width periodically across the flat substrate.

In some embodiments, a dual-functional adhesive textured surface may include three microstructured patterns of different dimensions arranged hierarchically wherein at least one of the microstructured patterns is dual-functional or the hierarchical combinations creates a dial-functional aspect. The article may consist of a flat substrate layer. On top of the substrate layer may be embossed solid pillars in a uniformly space square array. On top of each pillar in the first pattern of pillars may be embossed 1 to 10 solid cylinders of a smaller dimension. The cross-sectional profile of the first pillars may vary from circular to oval in a spatially periodic fashion.

In some embodiments, a dual-functional adhesive textured surface may include three microstructured patterns of different dimensions arranged hierarchically wherein at least one of the microstructured patterns may be dual-functional or the hierarchical combinations may create a dual-functional aspect. In particular, the embodiment may consist of a substrate layer with a sinusoidal aspect that varies in height from 50 to 500 microns.

Furthermore, the top of the substrate layer may be embossed with solid cylinders in a uniformly space square array. On top of each cylinder in the first pattern of cylinders may be embossed 1 to 10 solid cylinders of a smaller dimension. The height of the first cylinders may vary periodically across the substrate.

Some embodiments of the present disclosure may include a microstructure surface wherein the dual-functional surface may include three microstructured patterns of different dimensions arranged hierarchically. At least one of the microstructured patterns may be dual-functional or the hierarchical combinations creates a dial-functional aspect. first microstructure pattern may include a flat substrate layer, and a second microstructure pattern may be disposed on top of the substrate layer with embossed first solid pillars in a spatially varying square array. A third microstructure pattern may be disposed on top of each first solid pillars in the second pattern and may embossed 1 to 10 solid cylinders of a smaller dimension. The first microstructure pattern may include the arrangement of the first pillars in at least one region which may include a spacing corresponding to at least one of a concave, convex, v-saddle or h-saddle distribution as illustrated in FIG. 4.

At least one embodiment of the present disclosure includes a certain geometry of the microstructure features. Typical geometrical features may consist of rectangles, pyramids, mushroom shapes, cylinders with spatulate ends, hooks, coil, dished, and the like. Hierarchical structures may be constructed by stacking one geometrical pattern on top of a prior geometrical pattern. For example, pyramids with solid cylinders projecting vertically from the faces of the pyramids. Deformable geometries may be employed, for example, parallel ridges which under compression may form tunnels or circular concentric ridges that under compression may form narrower openings. Ridges arranged in a hexagonal grid display may exhibit exceptional adhesive properties.

It will be understood that in some embodiments, hierarchical structures can be constructed using a uniform square grid of solid cylinders of varying height, such that groups of solid cylinders may form pyramidal structures. In such structure constructions at least one feature may have a dual periodicity, for example, a spacing that may be constant and an orientation that varies.

In some embodiments of the present disclosure, combining dual functionality with other adhesive techniques may be used. For example, the inclusion of a chemical or viscous adhesive may be implemented. The use of suction cups that primarily work by creating a vacuum may be used rather than capillary action. Solid adhesives, such as fiber Gecko structures may be used. Such adhesives may create adhesion between the solid of the microstructured surface and a dry surface via van der Waals forces, on a target surface that typically may be wet at some later time.

In some embodiments, the microstructured multi-functional surfaces may be more adhesive when wet or in the presence of a surfactant or hydrophobic liquid, such as oil. The combination of a Wenzel-Cassie localization effect with respect to macroscopic aspects of a surface and an engagement aspect with respect to microscopic features may be used. When using an implant device, the micro features may be nomadic cells, and the macroscopic aspect may immobilize the implant allowing the cells to organize naturally and build biologic structures without disruption. Disruption may lead to fibrosis and less functional tissue associated with the implant. In a healing implant device, such as a hernia mesh, the tissue associated with the implant may help to reinforce the hernia defect, but may not promote growth of new muscle tissue which would represent a true healing of the hernia defect.

A Wenzel-Cassie interface may include a mixed interface, for example of water and soap, which may increase both peel force and translational force. By adding a lubricant to an interface between a capillary Wenzel-Cassie surface and a target surface, increased adhesivity may result. Furthermore, almost all aqueous environments involve both hydrophobic and hydrophilic components. For example, water-oil emulsions may be encountered in many external environments. Water-lipid emulsions may be encountered in most biological environments. Even skin to surface environments, where high humidity is present, may be considered hydrophilic-hydrophobic interfaces for the purposes of this disclosure.

Some embodiments may include non-slip surfaces for beverage containers, various skin contacting surfaces such as bandages or industrial equipment where a sure grip may be required. The combination of Wenzel-Cassie microstructured surfaces acting at one scale and other Wenzel-Cassie structures superimposed on the first structure but at a different scale may be particularly useful in environments where the target contact surface is variable.

It will be understood that embodiments of this disclosure do not rely on contact frictional force. Frictional forces may include direct mechanical interlocking of surface textures, such that for translation to occur one structure must fail structurally. Devices that rely on contact friction may be generally irritating when applied to living surfaces such as skin, or cause wear when applied to material surfaces. One adverse effect of contact friction is the formation of particulate. For example, in medical applications where attachment is desired, the formation of microscopic debris can be more harmful to the patient than the failure of the device. In the current disclosure, direct mechanical contact may be avoided or at most may be a secondary effect in localization. The application of large normal forces to achieve adhesivity may be specifically avoided. A transient minimal normal force may be permissible in most applications if such normal force results in a non-mechanically interlocking fixation state. However, when a multi-functional surface is employed, that one surface texture aspect may have a frictional component greater than other surface texture aspects. While friction may not be preferred in biological applications, a frictional aspect may be usefully employed in combination with the teachings disclosed here in some industrial and environmental applications. For example, some embodiments may include a hierarchical pillar arrangement (pillars on top of pillars) wherein the spacing between the pillars may be made particularly wide, 100-1000 microns, and the height of the pillars may vary across a range of 50-200 microns. An appreciable frictional aspect may be achieved by varying the pillar heights without affecting the Wenzel-Cassie zones achieved on each pillar-on-pillar structure.

An aspect of the present disclosure that will be appreciated by one of skill in the art relates to the adaptability to a target surface. In some embodiments, it may be desirable for the interface to resist normal force but not to prevent it. For example, for fingers in contact with a beverage container, one may not want the sensation of stickiness or abrasiveness. The sensation of stickiness may be due to chemical attachments that persist after the surface interface is broken. Stickiness may be specifically avoided in the present disclosure. It will be understood that there may be a clear delineation between immobilization and mobilization, and at the same time the threshold to achieve mobilization may be enhanced. On the other hand, another aspect of stickiness may be immediate maximum adhesion. In a mechanical translation, stickiness may be detrimental when a fluid motion is impeded by an over aggressive adhesion modality. An aspect of the present disclosure is that the adhesivity increases over time, and this period of latency may be adjustable. But in general, if adhesivity is dependent on fluid transport, such as in the case for capillary action, then the sensation of stickiness may generally be avoided.

In some embodiments a surface needs to be placed and then repositioned without harm to the target surface. The adhesivity may be an effect that builds over time based on the ordering of molecular constituents at the microstructure surface target surface interface. There may be additional benefits, for example, since surfaces of the present disclosure, especially those surfaces that are elastomeric, may tend to arrange their surface with respect to the target surface. Interfacing with irregular surfaces may require this accommodative effect, something seldom experienced with visco-adhesive surfaces that stick wherever they may make first contact. There may be considerable advantage in a surface that adheres to another surface in a way that their interface does not result in localized stresses, wrinkles, or folds. Hence, modulating the height of hierarchical structures, provided the modulus of the substrate material is sufficiently low, may lower frictional effects will ensuring uniform contact between the textured surface and the target surface.

In some regions, shear translations may be prevented, and in other regions, peel translations may be prevented, and in still other regions both effects may be required. In some embodiments, it may be desired that in some regions shear translations may be promoted with minimal force, and still other regions the peel force may be minimized. Applications of superhydrophobic surfaces are well known in the repulsion of other surfaces. Such surface patterns may also have minimal peel force. Any of these other classes of microstructured surfaces, meant to repel rather than attract, may be compatible with the surfaces of the present disclosure. It is an advantageous feature of microstructure patterning that most effects, including those described here, may be locally dependent on the pattern structure. Therefore, it is within the scope of the present disclosure to include capillary Wenzel-Cassie surfaces alongside more traditional superhydrophobic surfaces to achieve both repulsive and adhesive effects in one embodiment. Such structures may be useful in filtering particulate from solutions, chemical contaminants from solutions, and/or promoting the attachment of beneficial entities, be they living structures or chemical structures.

In some embodiments, microstructured hydrophobic-hydrophilic surfaces may be arranged both in scale and position, here called multi-functional hierarchical, to create zones of electrical, molecular, and polar order that may establish direct contact minimizing localizing interfaces. These surfaces may create a zone of exclusion between the microtextured surface and the interfacial liquid adherent to a target surface. The microstructured surfaces of the present disclosure may be locally anti-entropic, in the sense that decreasing the entropy of the interfacial zone may be achieved by raising the entropy in the system as a whole. This interaction has been overlooked by the prior art since the adhesion between two surfaces can be increased by increased order, even though the entire system may be less disordered. Localization of order may be one of the many features that provides the characteristics of the present disclosure. Similar to the capillary effect, the exclusion of solutes from a water volume may be accomplished by promoting a structure within the water that may be fundamentally hexagonal. Thus, the microstructure surfaces may promote hexagonal ordering of water which may exclude non-water constituents and promote hydrophilic-hydrophobic segregation by the structuring of water. This may result in a surface that structures water and minimizes the disruption of such structure. The surface texture may be considered a mediator of the water exclusive zone effect. While this effect may not be required for a Wenzel-Cassie structure, the exclusive zone effect may dramatically increase the stability of the Wenzel-Cassie structure on entropic grounds.

Some embodiments of the present invention may include a multi-functional microstructured surface comprised of at least two microstructured patterns of different dimensions arranged hierarchically wherein at least one of the effects may be due to the microstructured patterns and the hierarchical arrangement. At least one of the effects of the microstructured patterns may be due to a modulation of that hierarchical pattern along some dimension or geometry.

Some embodiments of the present invention may include a multi-functional microstructured surface which includes three microstructured patterns of different dimensions arranged hierarchically wherein at least one of the microstructured patterns may be varied periodically or the hierarchical arrangement as a whole may be varied periodically. In particular, some embodiments consist of a substrate layer onto which is embossed a two-dimensional pattern in such a way that both sides of the substrate layer may exhibit a sinusoidal aspect. Furthermore, on top of the sinusoidal substrate layer may be embossed solid cylinders filling each complete square cycle of the sinusoidal pattern with between 10 and 100 equally spaced cylinders. On top of each cylinder in the first pattern of cylinders may be embossed 1 to 10 solid cylinders of a smaller dimension. Wherein the first and second layers of pillars may create a zone of exclusion and a microstructured water state. The multi-functional effect may be achieved by modulating the microstructure surface in at least one dimensional or geometrical aspect. For example, the pillars could vary across the surface from circular cross section to rectangular cross section.

Some embodiments may include a multi-functional microstructured adhesive surface that may include three microstructured patterns of different dimensions arranged hierarchically wherein at least one of the microstructured patterns may be suctional or the hierarchical combinations may create a suctional aspect. The embodiment may consist of a flat substrate layer. On top of the substrate layer may be embossed solid cylinders in a uniformly space square array. On top of each cylinder in the first pattern of cylinders may be embossed 1 to 10 solid cylinders of a smaller dimension. The interstitial areas between the first layer of pillars may include drilled cylindrical holes, which may be drilled through the substrate layer, or only partially drilled through. The diameter of these holes may vary sinusoidally across the pattern surface in two dimensions. The capillary effect may be initiated by placing the microstructure surface on the fluid layer of the target surface without any applied pressure.

The first hierarchical cylinders may draw water away from the target surface sufficiently that the water comes into contact with the negative features comprising the drilled holes. The drilled holes may then apply a second capillary effect, which draws the microstructure layer into intimate contact with the target surface.

Some embodiments may include a multi-functional microstructured surface that may include three microstructured patterns of different dimensions arranged hierarchically wherein at least one of the microstructured patterns is a series of ridges arranged at equidistant intervals. In particular, the embodiment may include a flat substrate layer.

Furthermore, on top of the substrate layer may be embossed solid ridges in a uniformly spaced array. On top of each ridge in the first pattern of ridges may be embossed solid cylinders of a smaller dimension. In the interstitial areas between the first layer of ridges may be second solid cylinders. The first pattern of ridges may be curvilinear describing sinusoids equally spaced apart.

Some embodiments may include a multi-functional microstructured surface comprised of microstructured patterns of different dimensions arranged hierarchically wherein at least one of the microstructured patterns may be a stressed pattern. In particular, the stressed pattern may be a chiral stressed pattern.

Figure 13:
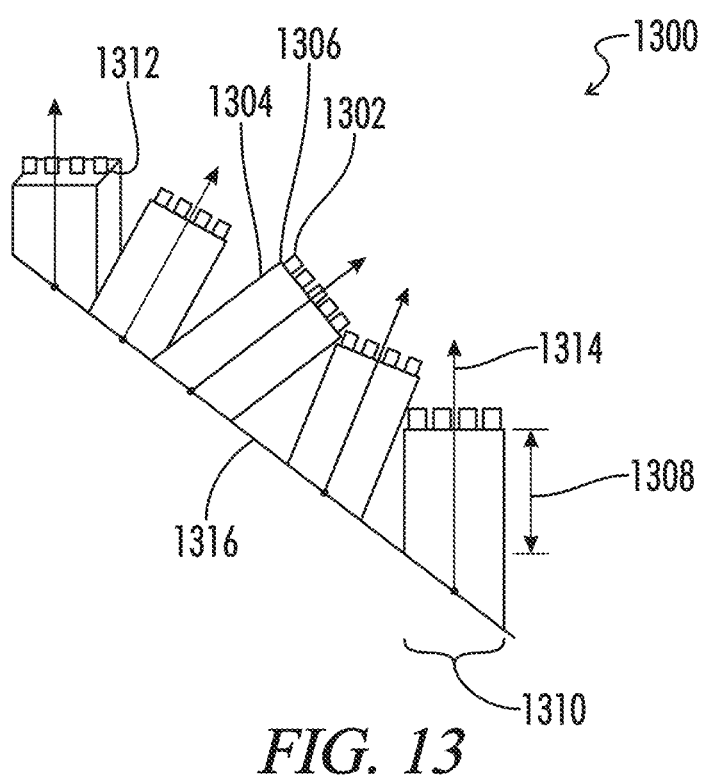
FIG. 13 is an embodiment of a microstructured surface of the present disclosure.

Referring now to FIG. 13, a microstructured surface 1300 comprises at least two kinds of microstructured features. The lateral aspect ratio of the features may range from about 0.1 to about 10 for each feature, and at least one feature dimension may vary by at least a factor of 10%. Microstructured surface 1300 may include two sets of pillars 1302 and 1304. Pillars 1302 may be 5 microns in diameter and 30 microns tall and pillars 1304 may be at least 15 microns in diameter and at least 75 microns tall. The first set of pillars 1302 may be disposed on the top surface 1306 of the second set of pillars 1304. At least two of the feature dimensions (height 1308, width 1310, length 1312, orientation 1314) must be microscopic. All three of the feature dimensions (height, width, length) may be microscopic. The dual functionality may be achieved by varying one or more of the parameters across the surface 1316 of the device 1300. The variation may be spatially periodic, or within a statistical range. A modulation aspect is a patterned feature, usually periodic, that affects a contact surface at a different scale than the underlying hierarchical structure.

Figure 14:
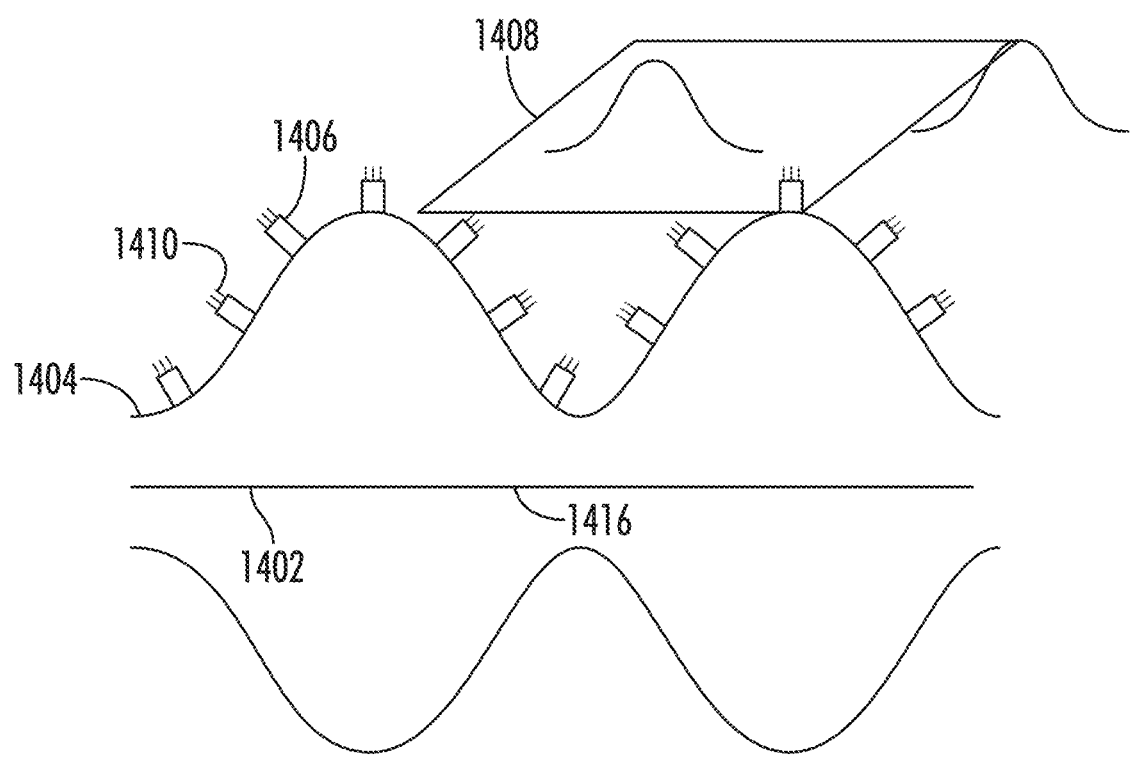
FIG. 14 is an embodiment consisting of a substrate layer onto which is embossed a two-dimensional pattern.

Referring to FIG. 14, a dual-functional surface 1400 may include at least two microstructured patterns of different dimensions arranged hierarchically wherein at least one of the microstructured patterns is dual functional or the hierarchical combinations create a dual-functional aspect. In particular, some embodiments may include a substrate layer 1402 onto which is embossed a two-dimensional pattern 1404 in such a way that both sides of the substrate layer 1402 may exhibit a sinusoidal aspect.

Furthermore, on top of the sinusoidal substrate layer 1404 may be embossed solid cylinders 1406 filling each complete square cycle 1408 of the sinusoidal pattern 1404 with between 10 and 100 equally spaced cylinders. On top of each cylinder 1406 in the first pattern of cylinders may be embossed 1 to 10 solid cylinders 1410 of a smaller dimension. The dual-functional effect may be initiated by modulating the first cylinder orientations 1414 with respect to a virtual flat surface 1416. In particular, the first cylinders may be oriented perpendicular to the sinusoidal surface.

Figure 15:
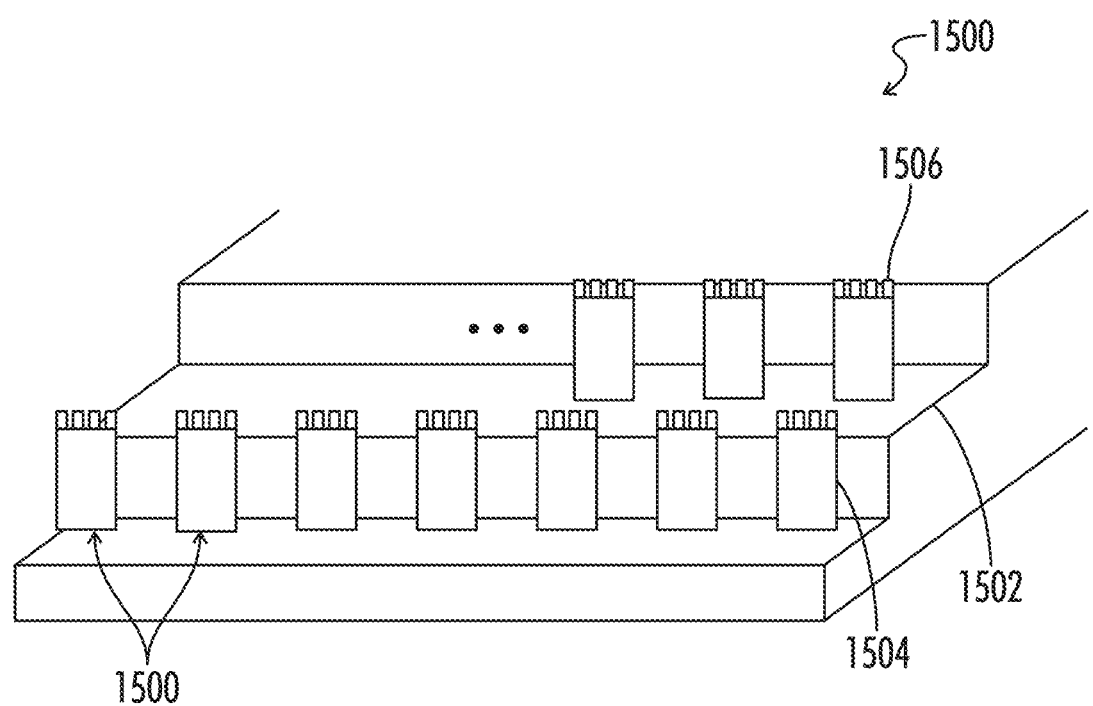
FIG. 15 is an embodiment consisting of a substrate having a stepped surface.

Referring to FIG. 15, a dual-functional patterned surface 1500 may include three microstructured patterns of different dimensions arranged hierarchically wherein at least one of the microstructured patterns is dual-functional or the hierarchical combinations creates a dual-functional aspect. In particular, some embodiments may include a stepped flat substrate layer 1502. Furthermore, on top of the substrate layer 1502 may be embossed solid cylinders 1504 in a uniformly spaced square array. On top of each cylinder 1504 in the first pattern of cylinders may be embossed 1 to 10 solid cylinders 1506 of a smaller dimension. The first cylinders 1504 may vary in width 1508 periodically across the flat substrate.

Figure 16:
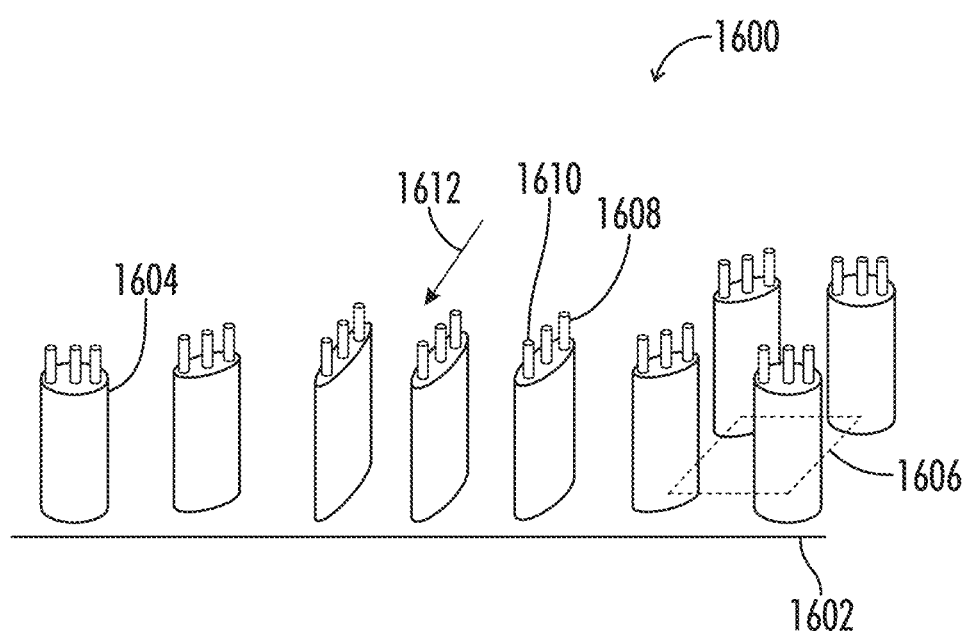
FIG. 16 is an embodiment consisting of a hierarchical microstructure array having varying cross-sectional profiles from circular to oval in a spatially periodic fashion.

Referring to FIG. 16, a dual-functional surface 1600 may include three microstructured patterns of different dimensions arranged hierarchically wherein at least one of the microstructured patterns is dual-functional or the hierarchical combinations creates a dial-functional aspect. In particular, some embodiments may include a flat substrate layer 1602. Furthermore, on top of the substrate layer 1602 may be embossed solid pillars 1604 in a spatially varying square array 1606. On top of each pillar 1604 in the first pattern of pillars may be embossed 1 to 10 solid cylinders 1608 of a smaller dimension. The cross-sectional profile of the first pillars 1604 may vary from circular 1610 to oval 1612 in a spatially periodic fashion as illustrated in FIG. 3.

Those embodiments described above are provided to clarify the present invention to enable the ordinary person skilled in the art to understand, make, and use the present invention. However, it is not intended to limit the scope of the present invention, and any equivalent modification and variation according to the spirit of the present invention is to be also included within the scope of the present invention.

Thus, although there have been described particular embodiments of the present invention of a new and useful Multifunctional Textured Device it is not intended that such references be construed as limitations upon the scope of this invention except as set forth in the following claims.

What is claimed is:

1. A microstructured surface comprising:
a substrate having a microstructure pattern comprising a plurality of first set of microstructure features and a plurality of second set of microstructure features, the plurality of first set of microstructure features being disposed about the substrate and having a spacing between adjacent microstructure features from 100-1000 microns, the plurality of second set of microstructure features being smaller than the first set of microstructure features and disposed hierarchically on the plurality of first set of microstructure features, and wherein at least one of the plurality of first set of microstructure features or the plurality of second set of microstructure features includes a width that varies periodically across the substrate;

wherein the plurality of first set of microstructure features comprise a cross sectional profile varies periodically from circular to oval across the substrate, such that the variation repeats across the x-axis and y-axis of the substrate creating a modulated pattern, and wherein the microstructure pattern is configured to generate a Wenzel Cassie wetting state when interacting with a target surface and a fluid.

2. The microstructured surface of claim 1 wherein the substrate is flat and the plurality of first set of microstructure features are disposed about the flat substrate.

3. The microstructured surface of claim 1 wherein the plurality of second sets of microstructure features have a geometrical shape selected from the group consisting of rectangles, pyramids, mushroom shapes, cylinders with spatulate ends, hoods, coil, dished, and solid cylinders.

4. The microstructure surface of claim 1 wherein the plurality of first set of microstructure features having a height from 50-200 microns.

5. A microstructured surface comprising:
a substrate having a surface, the surface including a microstructure pattern comprising a plurality of first set of microstructure features, and a plurality of second set of microstructure features, the plurality of first set of microstructure features being disposed about the substrate and having a spacing between adjacent microstructure features from 100-1000 microns, a height of the plurality of first set of microstructure features from 50-200 microns, the plurality of second set of microstructure features being smaller than the first set of microstructure features and disposed hierarchically on the plurality of first set of microstructure features;

wherein the plurality of first set of microstructure features comprises a width that varies periodically across the substrate, such that the variation repeats across the x-axis and y-axis of the substrate creating a modulated pattern; and wherein the microstructure pattern is configured to produce a Wenzel-Cassie wetting state when interacting with a target surface and a fluid.

6. The microstructured surface of claim 5 wherein the plurality of first set of microstructure features are solid cylinders.

7. The microstructure surface of claim 5 wherein the plurality of second set of microstructure features are solid cylinders.

8. The microstructured surface of claim 5 wherein the plurality of first and second sets of microstructure features have a geometrical shape selected from the group consisting of rectangles, pyramids, mushroom shapes, cylinders with spatulate ends, hoods, coil, dished, and solid cylinders.

* * * * *